United States Patent
Le Neel et al.

(10) Patent No.: US 9,082,681 B2
(45) Date of Patent: Jul. 14, 2015

(54) ADHESIVE BONDING TECHNIQUE FOR USE WITH CAPACITIVE MICRO-SENSORS

(71) Applicant: STMicroelectronics Pte Ltd., Singapore (SG)

(72) Inventors: Olivier Le Neel, Singapore (SG); Shian-Yeu Kam, Singapore (SG); Tien-Choy Loh, Singapore (SG); Ditto Adnan, Singapore (SG); Tze Wei Dennis Chew, Singapore (SG)

(73) Assignee: STMicroelectronics Pte Ltd., Singapore (SG)

( * ) Notice: Subject to any disclaimer, the term of this patent is extended or adjusted under 35 U.S.C. 154(b) by 0 days.

(21) Appl. No.: 13/853,886

(22) Filed: Mar. 29, 2013

(65) Prior Publication Data
US 2014/0291829 A1 Oct. 2, 2014

(51) Int. Cl.
| | |
|---|---|
| *H01L 21/44* | (2006.01) |
| *H01L 25/16* | (2006.01) |
| *H01L 21/56* | (2006.01) |
| *H01L 25/00* | (2006.01) |
| *G01N 27/22* | (2006.01) |

(52) U.S. Cl.
CPC .............. *H01L 25/16* (2013.01); *H01L 21/561* (2013.01); *H01L 25/00* (2013.01); *G01N 27/223* (2013.01); *H01L 2224/32145* (2013.01); *H01L 2224/48091* (2013.01); *H01L 2224/48145* (2013.01); *H01L 2224/73265* (2013.01); *H01L 2924/1815* (2013.01)

(58) Field of Classification Search
CPC ....................................................... G01C 19/00
USPC ....................... 438/51; 257/E21.499, E29.324
See application file for complete search history.

(56) References Cited

U.S. PATENT DOCUMENTS

| | | | |
|---|---|---|---|
| 6,243,474 | B1 | 6/2001 | Tai et al. |
| 6,478,974 | B1 | 11/2002 | Lebouitz et al. |
| 6,879,089 | B2 | 4/2005 | Wong et al. |
| 7,280,436 | B2 | 10/2007 | Pedersen |

(Continued)

FOREIGN PATENT DOCUMENTS

TW 200531224 A 9/2005

OTHER PUBLICATIONS

Wilson et al.,"APTI Course 435 Atmospheric Sampling Student Manual: ," United States Environmental Protection Agency, Air Pollution Training Institute, Research Triangle Park, N.C., Chapter 3, Air measuring instruments, pp. 3-1 to 3-56, Sep. 1980, 61 Pages.

(Continued)

*Primary Examiner* — Telly Green
(74) *Attorney, Agent, or Firm* — Seed IP Law Group PLLC (57) ABSTRACT

A micro-sensor device that includes a passivation-protected ASIC module and a micro-sensor module bonded to a patterned cap provides protection for signal conditioning circuitry while allowing one or more sensing elements in the micro-sensor module to be exposed to an ambient environment. According to a method of fabricating the micro-sensor device, the patterned cap can be bonded to the micro-sensor module using a planarizing adhesive that is chemically compatible with the sensing elements. In one embodiment, the adhesive material is the same material used for the dielectric active elements, for example, a photo-sensitive polyimide film.

15 Claims, 10 Drawing Sheets

(56) References Cited

U.S. PATENT DOCUMENTS

| | | | |
|---|---|---|---|
| 7,556,895 B2 | 7/2009 | Moriya et al. | |
| 7,821,085 B2 | 10/2010 | Suzuki et al. | |
| 7,864,403 B2 | 1/2011 | Bita et al. | |
| 7,880,315 B2 * | 2/2011 | Beyne et al. | 257/780 |
| 8,062,497 B2 | 11/2011 | Witvrouw et al. | |
| 8,258,017 B2 * | 9/2012 | Masuko et al. | 438/118 |
| 8,390,121 B2 | 3/2013 | Okumura et al. | |
| 8,487,387 B2 | 7/2013 | Lin et al. | |
| 8,715,514 B2 | 5/2014 | Lee et al. | |
| 2002/0160611 A1 | 10/2002 | Horsley | |
| 2008/0194053 A1 | 8/2008 | Huang | |
| 2008/0308920 A1 * | 12/2008 | Wan | 257/685 |
| 2008/0315332 A1 | 12/2008 | Kaelberer et al. | |
| 2009/0218702 A1 * | 9/2009 | Beyne et al. | 257/778 |
| 2010/0173437 A1 | 7/2010 | Wygant et al. | |
| 2010/0314740 A1 * | 12/2010 | Choi et al. | 257/686 |
| 2011/0031565 A1 * | 2/2011 | Marx et al. | 257/417 |
| 2011/0045639 A1 * | 2/2011 | Masuko et al. | 438/118 |
| 2011/0150261 A1 * | 6/2011 | Ho et al. | 381/361 |
| 2011/0298134 A1 * | 12/2011 | Williams et al. | 257/751 |
| 2012/0032283 A1 * | 2/2012 | Frey et al. | 257/415 |
| 2012/0167392 A1 | 7/2012 | Cherian et al. | |
| 2012/0168882 A1 | 7/2012 | Cherian et al. | |
| 2012/0171713 A1 | 7/2012 | Cherian et al. | |
| 2012/0171774 A1 | 7/2012 | Cherian et al. | |
| 2012/0299127 A1 | 11/2012 | Fujii et al. | |
| 2013/0010826 A1 | 1/2013 | Le Neel et al. | |
| 2013/0139587 A1 | 6/2013 | Le Neel et al. | |
| 2013/0334620 A1 | 12/2013 | Chu et al. | |
| 2014/0264655 A1 | 9/2014 | Williams et al. | |
| 2014/0264744 A1 | 9/2014 | Chi et al. | |
| 2014/0268523 A1 | 9/2014 | Gogoi | |

OTHER PUBLICATIONS

J.M Lim, B.H. Yoon, Y.K Oh, Kyung-Am Park, "The humidity effect on air flow rates in a critical flow venturi nozzle," Flow Measurement and Instrumentation, 22:402-405, Jun. 4, 2011, 4 Pages.

Le Neel et al., "Microelectronic Enviromental Sensing Module," U.S. Appl. No. 13/853,801, Mar. 29, 2013, 37 Pages.

Le Neel et al., "Durable Minature Gas Composition Detector Having Fast Response Time," U.S Appl. No. 13/853,805, Mar. 29, 2013, 36 Pages.

Le Neel et al., "Integrated Multi-Sensor Module," U.S. Appl. No. 13/853,732, Mar. 29, 2013, 37 Pages.

Loh et al., "Method for Forming a Suspended Membrane," U.S. Appl. No. 13/907,708, May 31, 2013, 31 Pages.

* cited by examiner

Fig. 10 ued herein for purposes of...

ADHESIVE BONDING TECHNIQUE FOR USE WITH CAPACITIVE MICRO-SENSORS

BACKGROUND

1. Technical Field The present disclosure relates to the fabrication and electronic packaging of miniature environmental sensors.

2. Description of the Related Art

With the advent of micro-mechanical systems, deployment of sensors and feedback control systems in smaller scale applications is made possible. For instance, many electronic devices now contain environmental sensors. In one example, electronic thermostats connected to climate control systems rely on temperature sensors to trigger activation of furnaces and air conditioners. In another example, electronic weather stations rely on internal temperature sensors, barometric pressure sensors, and humidity sensors.

Miniature sensors that are typically embedded on board mobile computing devices such as smart phones and tablet computers include, for example, magnetic field sensors used to determine orientation of a smart phone relative to the earth's magnetic field. Providing additional environmental micro-sensors within smart phones, tablet computers, and the like may encourage program developers to create applications that otherwise might not be possible. Such micro-sensors require very small dimensions to be suitable for use in mobile electronic devices. For example, the micro-sensors can be manufactured using 1-micron feature sizes on a semiconductor die size of about 1-3 square millimeters. In addition, such micro-sensors typically require signal processing circuitry that can be manufactured as application-specific integrated circuits (ASICs) having feature sizes in the range of about 10-100 nm.

BRIEF SUMMARY

Because the feature sizes of environmental micro-sensors are so much larger than those of associated ASICs, the sensors and the ASICs can be manufactured separately as different integrated circuit products on different substrates. After sawing the substrates, individual IC modules can then be assembled into a common package. However, while the ASICs, like most integrated circuits, need protection from environmental elements such as extreme temperatures, pressure fluctuations, and humidity, at least portions of the micro-sensors must be exposed to the environment to accurately sense ambient environmental conditions.

A micro-sensor device that includes a passivation-protected ASIC module and a micro-sensor module bonded to a patterned cap provides protection for the signal conditioning circuitry in the ASIC module, while allowing one or more sensing elements in the micro-sensor module to be exposed to the ambient environment. The patterned cap can be bonded to the micro-sensor module using a planarizing adhesive that is chemically compatible with the sensing elements. In one embodiment, the adhesive material is the same material used for the dielectric active elements, for example, a photo-sensitive polyimide film.

BRIEF DESCRIPTION OF THE SEVERAL VIEWS OF THE DRAWINGS

In the drawings, identical reference numbers identify similar elements. The sizes and relative positions of elements in the drawings are not necessarily drawn to scale.

DETAILED DESCRIPTION

It will be appreciated that, although specific embodiments of the present disclosure are described herein for purposes of illustration, various modifications may be made without departing from the spirit and scope of the present disclosure. Accordingly, the present disclosure is not limited except as by the appended claims.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

In the following description, certain specific details are set forth in order to provide a thorough understanding of various aspects of the disclosed subject matter. However, the disclosed subject matter may be practiced without these specific details. In some instances, well-known structures and methods of semiconductor processing comprising embodiments of the subject matter disclosed herein have not been described in detail to avoid obscuring the descriptions of other aspects of the present disclosure.

Reference throughout the specification to insulating materials or semiconducting materials can include various materials other than those used to illustrate specific embodiments of the devices presented. For example, the term "substrate" should not be construed narrowly to limit a substrate to silicon or gallium arsenide, or even a semiconductor substrate for example. Rather, the term "substrate" is broadly construed to cover any supporting material on which a circuit is formed or fabricated.

Reference throughout the specification to conventional thin film deposition techniques for depositing silicon nitride, silicon dioxide, metals, or similar materials include such processes as chemical vapor deposition (CVD), low-pressure chemical vapor deposition (LPCVD), metal organic chemical vapor deposition (MOCVD), plasma-enhanced chemical vapor deposition (PECVD), plasma vapor deposition (PVD), atomic layer deposition (ALD), molecular beam epitaxy (MBE), electroplating, electroless plating, and the like. Specific embodiments are described herein with reference to examples of such processes. However, the present disclosure and the reference to certain deposition techniques should not be limited to those described. For example, in some circumstances, a description that references CVD may alternatively be done using PVD, or a description that specifies electroplating may alternatively be accomplished using electroless plating. Furthermore, reference to conventional techniques of thin film formation may include growing a film in situ. For example, in some embodiments, controlled growth of an oxide to a desired thickness can be achieved by exposing a silicon surface to oxygen gas or to moisture in a heated chamber.

Reference throughout the specification to conventional photolithography techniques, known in the art of semiconductor fabrication for patterning various thin films, include a spin-expose-develop process sequence involving a photoresist. Such a photolithography sequence entails spinning on the photoresist, exposing areas of the photoresist to ultraviolet light through a patterned mask, and developing away exposed (or alternatively, unexposed) areas of the photoresist, thereby transferring a positive or negative mask pattern to the photoresist. The photoresist mask can then be used to etch the mask pattern into one or more underlying films. Typically, a photoresist mask is effective if the subsequent etch is relatively shallow, because photoresist is likely to be consumed during the etch process. Otherwise, the photoresist can be used to pattern a hard mask, which in turn, can be used to pattern a thicker underlying film.

Reference throughout the specification to conventional etching techniques known in the art of semiconductor fabrication for selective removal of polysilicon, silicon nitride, silicon dioxide, metals, photoresist, polyimide, or similar materials include such processes as wet chemical etching, reactive ion (plasma) etching (RIE), washing, wet cleaning, pre-cleaning, spray cleaning, chemical-mechanical planarization (CMP) and the like. Specific embodiments are described herein with reference to examples of such processes. However, the present disclosure and the reference to certain deposition techniques should not be limited to those described. In some instances, two such techniques may be interchangeable. For example, stripping photoresist may entail immersing a sample in a wet chemical bath or, alternatively, spraying wet chemicals directly onto the sample.

Specific embodiments are described herein with reference to examples of integrated micro-sensors that have been produced; however, the present disclosure and the reference to certain materials, dimensions, and the details and ordering of processing steps are exemplary and should not be limited to those shown.

In the figures, identical reference numbers identify similar features or elements. The sizes and relative positions of the features in the figures are not necessarily drawn to scale.

Figure 1:
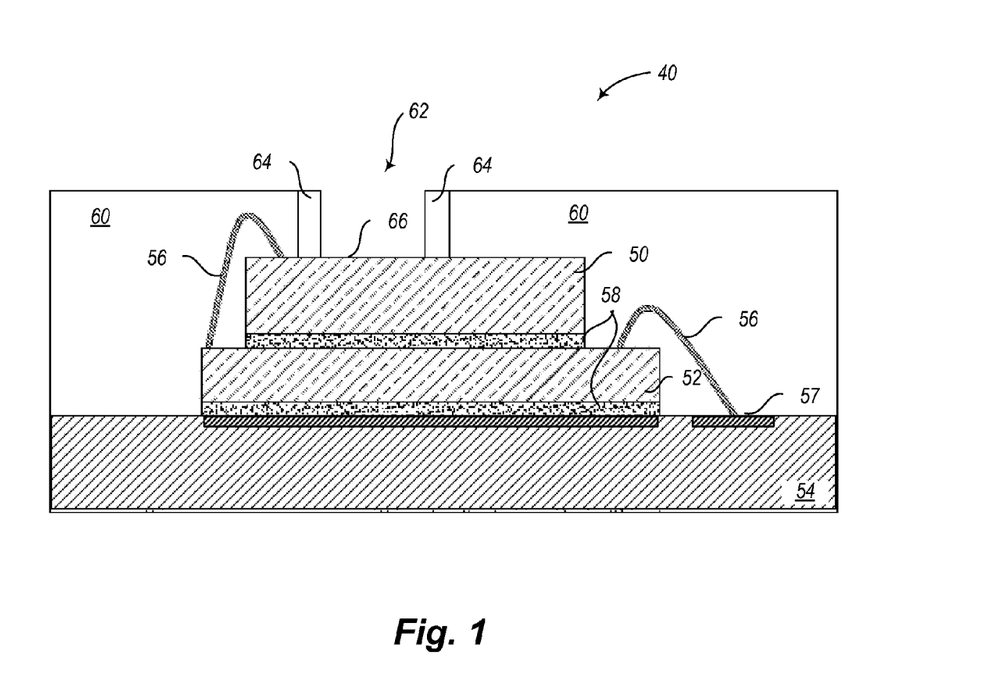
FIG. 1 is a side view of one embodiment of a micro-sensor module and an ASIC module assembled into a molded electronic package.

FIG. 1 shows one embodiment of a micro-sensor device 40 in which a micro-sensor module 50 is coupled to an application-specific integrated circuit (ASIC) module 52 and a substrate 54 by wire bonds 56. The micro-sensor module 50 and the ASIC module 52 can be stacked on the substrate 54. The substrate 54 can be a standard printed circuit board substrate made of, for example, a polymer-based insulating material. The wire bonds 56 can attach to the substrate 54 at a metal bond pad 57. Likewise, the ASIC module 52 can attach to the substrate 54 at a metal bond pad 57. A layer of adhesive 58 can be used to separate the micro-sensor module 50 from the ASIC module 52. The adhesive 58 can be, for example, a die film attach (DAF) adhesive material, available from the Dow Corning Corporation of Midland, Mich. An epoxy molding compound 60 encapsulates the ASIC and the wire bonds 56, while leaving an opening 62 over the micro-sensor module 50. A physical ring 64 surrounds a micro-sensor on a top surface 66 of the micro-sensor module 50. The physical ring 64 provides a barrier to prevent the epoxy molding compound 60 from coming into contact with active areas of the micro-sensor module 50. The physical ring 64 thus prevents residue from being left on sensing elements on the top surface 66 of the micro-sensor module 50. The physical ring 64 extends above the sensor substrate such that the sensor substrate is not planarized. Placement of the physical ring 64 can be performed at assembly level, but presents challenges regarding positioning accuracy and stress during the placement process. Furthermore, impurities in the epoxy molding compound 60 can be chemically incompatible with materials on the micro-sensor module 50 or the ASIC module 52.

Figure 2:
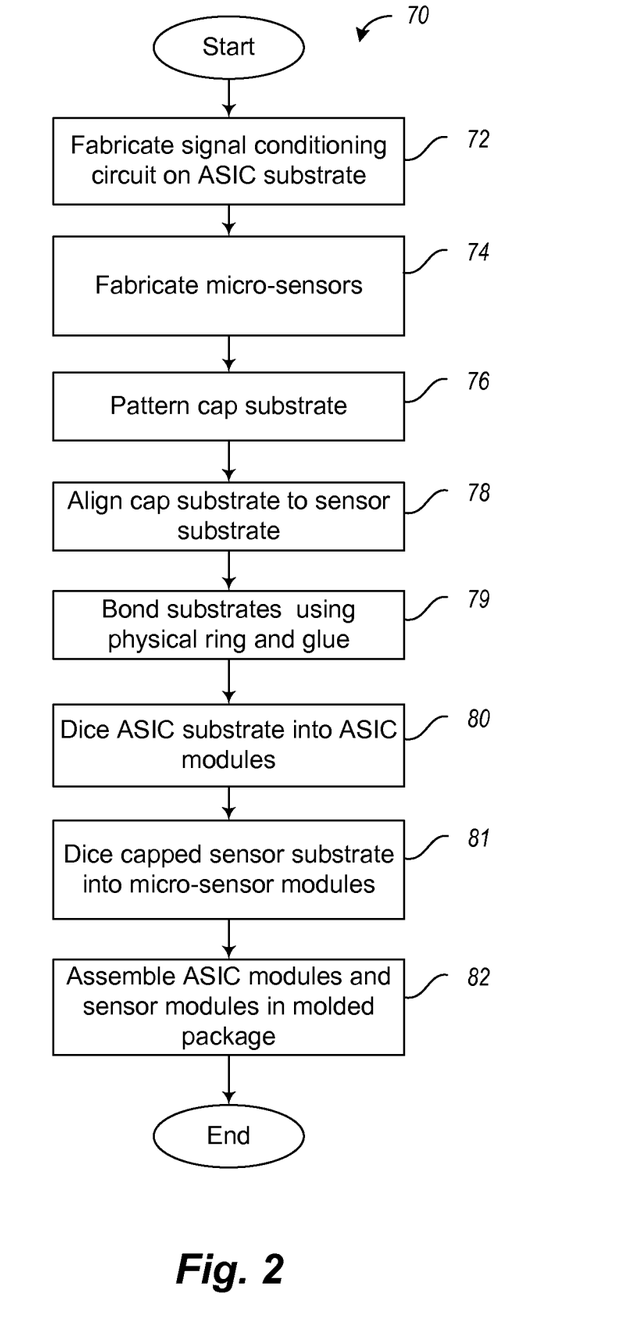
FIG. 2 is a high level flow diagram showing a sequence of steps in fabricating the micro-sensor device shown in FIG. 1.

With reference to FIG. 2, a high level sequence of processing steps 70 can be carried out to build and assemble the micro-sensor device 40 shown in FIG. 1.

At 72, the ASIC modules 52 for signal conditioning can be fabricated on an ASIC substrate according to a process technology having critical dimensions of about 28 nm.

At 74, the micro-sensor modules 50 can be fabricated on a sensor substrate according to a process technology having critical dimensions of about 1 micron.

At 76, a cap substrate can be patterned.

At 78 the cap substrate can be aligned to the sensor substrate.

The ASIC substrate can be sawed into individual ASIC modules 52.

At 79, the physical ring 64 can be placed, and the cap substrate and the sensor substrate can be bonded using glue (e.g., epoxy).

At 80, the ASIC substrate can be sawed into individual ASIC modules 52.

At 81, the capped sensor substrate can be sawed into individual capped micro-sensor modules 50.

At 82, an ASIC module 52 and a micro-sensor module 50 can be assembled into a molded package by stacking the micro-sensor and ASIC modules 52 on a substrate, wire-bonding the modules to the substrate and to one another, and using an epoxy molding compound 60 to encapsulate the stack.

Figure 3:
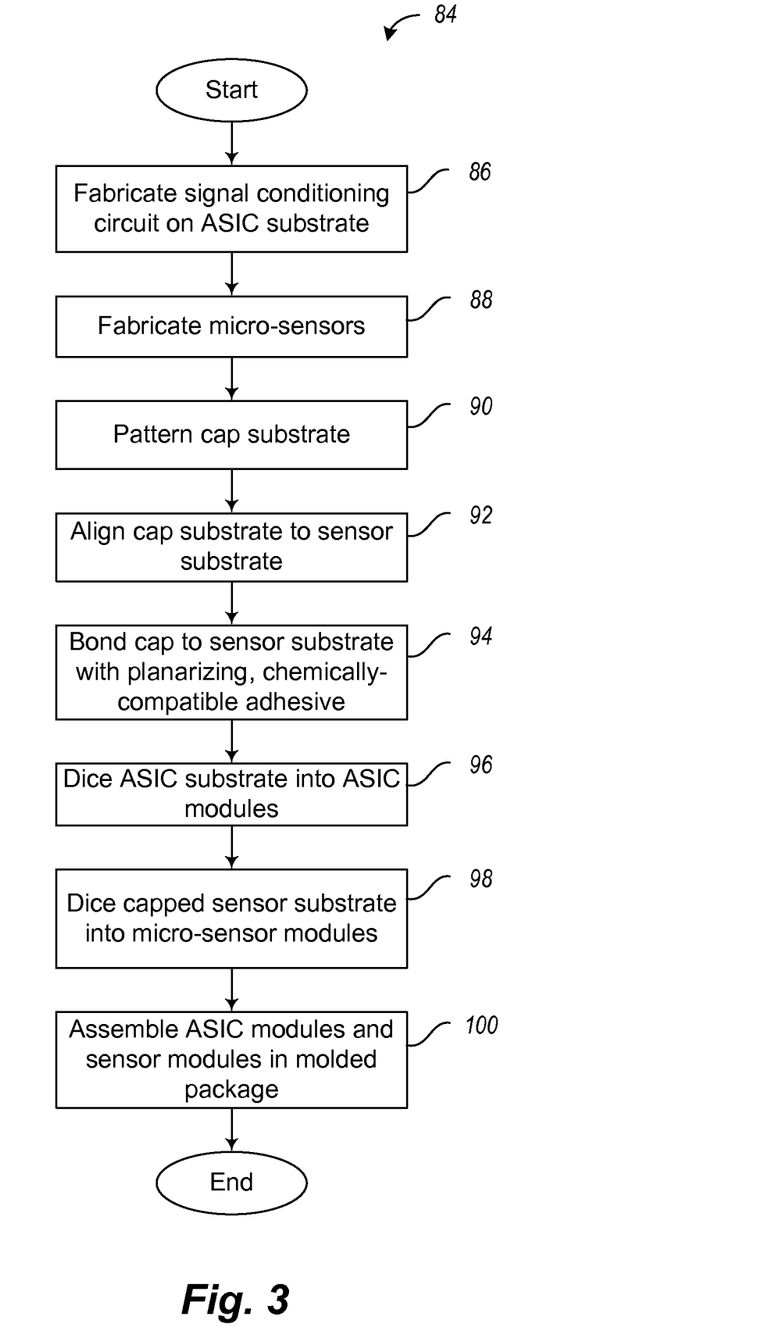
FIG. 3 is a high level flow diagram showing an alternative sequence of steps in fabricating an alternative micro-sensor device as described herein.

With reference to FIG. 3, a high level sequence of processing steps 84 can be carried out to build and assemble an alternative embodiment of a capped micro-sensor device as described herein, in which the cap is adhesively bonded to the micro-sensor module 50, using an adhesive material that provides chemical compatibility and also serves as a planarizing material. In this embodiment, a physical ring is not needed. The adhesive material overcomes some of the drawbacks of the sequence of processing steps 70 described above. The sequence of processing steps 84 proceeds as follows:

At 86, the ASIC modules 52 for signal conditioning can be fabricated on an ASIC substrate according to a processing technology having critical dimensions of about 28 nm.

At 88, the micro-sensor modules 50 can be fabricated on a sensor substrate according to the processing sequence described below with reference to FIG. 5, in particular.

At 90, a cap substrate can be patterned for use in protecting certain ones of the micro-sensor modules 50.

At 92, the cap substrate can be aligned to the sensor substrate.

At 94, the cap substrate can be adhesively bonded to the sensor substrate using a thick adhesive layer that planarizes the surface of the sensor substrate. The adhesive layer is desirably made of a material that is chemically compatible with the micro-sensor module.

At 96, the ASIC substrate can be sawed into individual ASIC modules 52.

At 98, the capped sensor substrate can be sawed into individual micro-sensor modules 50.

At 100, an ASIC module 52 and a capped micro-sensor module 50 can be assembled into a molded package.

Figures 4A, 4B, 4C:
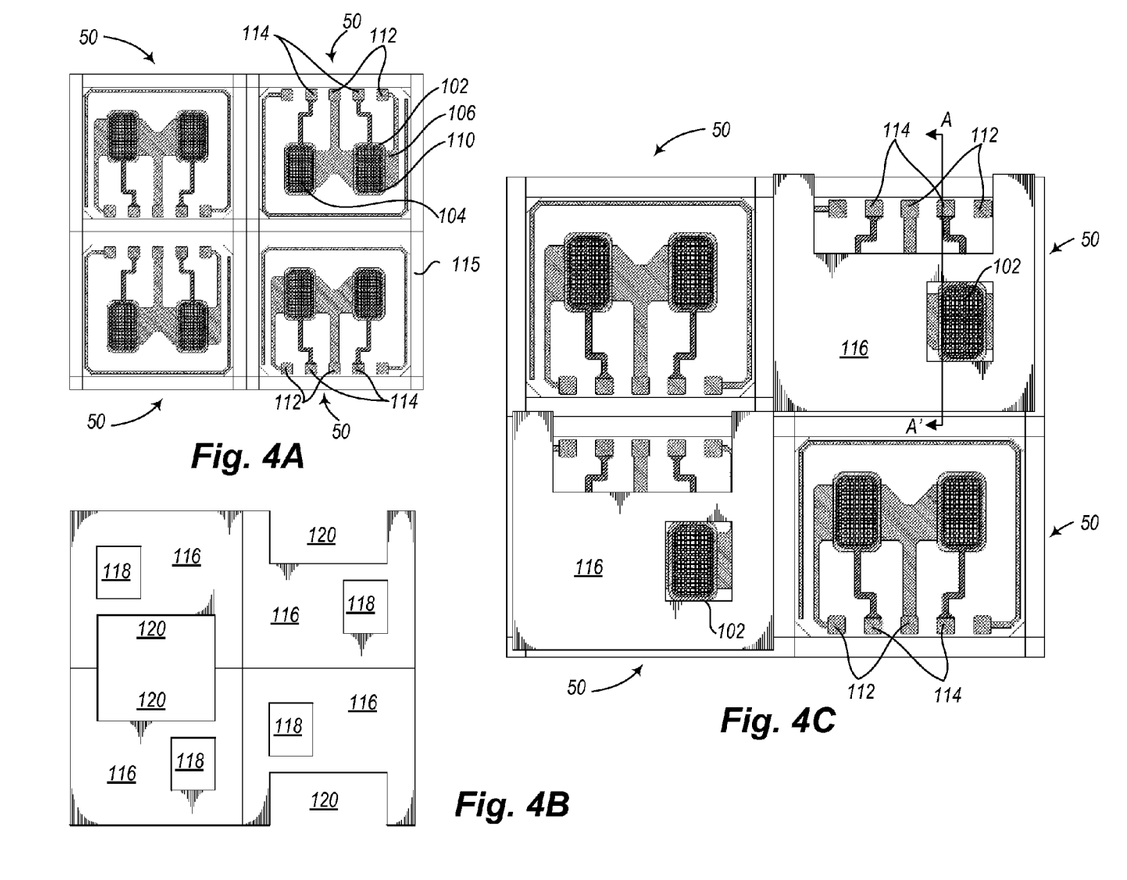
FIG. 4A is a top plan view of four micro-sensor modules, as described herein.
FIG. 4B is a top plan view of four caps, as described herein.
FIG. 4C is a top plan view of two of the caps shown in FIG. 4B bonded to two of the micro-sensor modules shown in FIG. 4A.

FIG. 4A shows a layout of four exemplary micro-sensor modules 50 in a mirror-image arrangement. Each of the micro-sensor modules 50 in the example shown includes a capacitive micro-sensor 102 and a reference micro-sensor 104 having a common bottom plate 106. The capacitive micro-sensor 102 can be, for example, a pressure sensor or a relative humidity sensor used to measure ambient environmental conditions. The reference micro-sensor 104 can be, for example, a reference pressure sensor. Additionally or alternatively, other types of micro-sensors can be included in the micro-sensor modules 50. Such micro-sensors may include, but are not limited to, resistive micro-sensors such as a miniature Wheatstone bridge for measuring ambient temperature as described in U.S. patent application Ser. No. 13/853,732; micro-sensors designed to measure gas flow (e.g., air flow) in the form of miniature Venturi chambers as described in U.S. patent application Ser. No. 13/853,801 or miniature Hall effect sensors for use in measuring gas concentrations (e.g., oxygen concentration within an air sample), as described in U.S. patent application Ser. No. 13/853,805. It is noted that each of the aforementioned patent applications is by the same applicant as the present patent application.

The micro-sensors 102 and 104 can be in the form of parallel plate capacitors in which the common bottom plate 106 is in contact with a dielectric active element 108. The dielectric active element 108 can be, in turn, in contact with a metal mesh top plate 110. The common bottom plate 106 can also serve as a heating element for use in calibrating the micro-sensors 102, 104 as described in U.S. patent application Ser. No. 13/853,732. The common bottom plate 106 can be electrically coupled to electrical contacts 112, and the metal mesh top plate 110 can be electrically coupled to electrical contacts 114. The electrical contacts 112 and 114 can be used to energize, or to collect data from, the micro-sensors 102 and 104. Around the perimeter of the layout shown in FIG. 4A there is provided a scribe line 115 along which the micro-sensor modules 50 can be cut and thereby separated from one another for placement of individual micro-sensor modules in an electronic package.

FIG. 4B shows a layout of four caps 116 in a mirror-image arrangement. The caps 116 can be cut from silicon substrates, for example. Openings in the caps 116 include sensor windows 118 and contact windows 120. The sensor windows 118 expose the dielectric active elements 108 to an ambient environment. The contact windows 120 expose electrical contacts 112 for receiving power to the common bottom plate 106, and electrical contacts 114 for transferring data from the micro-sensors 102 and 104.

FIG. 4C shows two of the four caps 116 from FIG. 1B (the upper right and lower left caps) superimposed on the layout of four exemplary micro-sensor modules 50 from FIG. 1A. The caps 116 are aligned with the micro-sensor modules 50 so as to expose the capacitive micro-sensors 102, while covering the reference micro-sensors 104.

Figure 5:
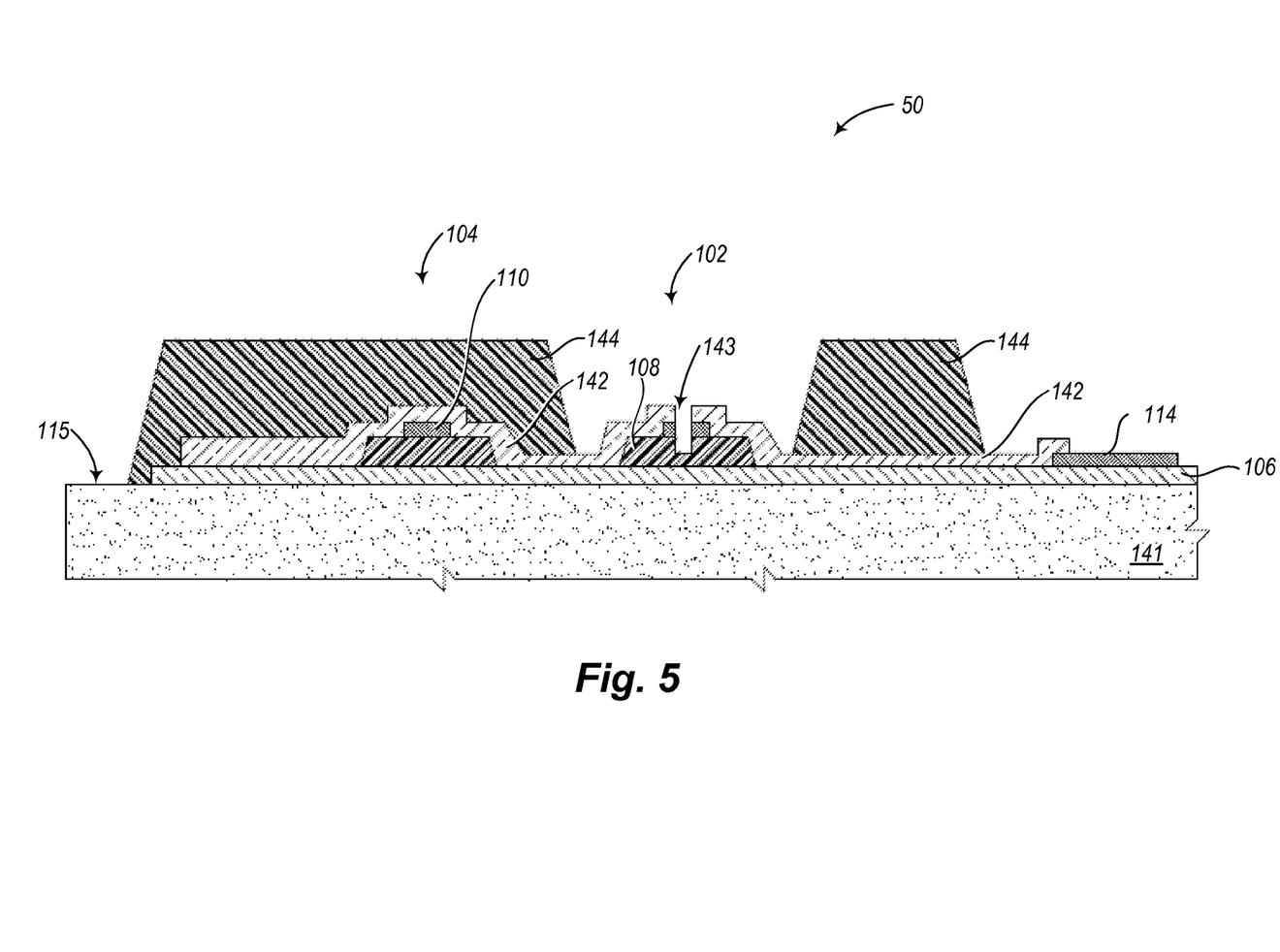
FIG. 5 is a cross-sectional view of an exemplary micro-sensor module shown in FIG. 4C.

FIG. 5 shows a cross-section of a representative micro-sensor module 50 shown in FIG. 1C, along cut lines A-A'. The micro-sensor module 50 includes the capacitive micro-sensor 102 and the reference micro-sensor 104 as fabricated on a silicon sensor substrate 141. A 1 µm thick layer of oxide (not shown) can be formed on the surface of the sensor substrate 141 by a standard deposition or oxide growth process. Layers of the micro-sensors 102 and 104 include the common bottom plate 106, dielectric active elements 108, and the metal mesh top plate 110.

The dielectric active elements 108 can be made of, for example, a 4 µm thick photosensitive polyimide film such as HD 8820, available from Hitachi Chemical Dupont Microsystems, Ltd. The exemplary HD 8820 polyimide is known to those skilled in the art of photolithography as a synthetic polymer consisting of monomer chains of p-phenylene-2 and 6-benzobisoxazole. The HD 8820 polyimide can be cured at a temperature of about 325° C., exposed to broadband UV light, and developed using an aqueous developer (e.g., a TMAH-based developer) to realize a desired pattern.

An electrical contact 114 is shown on the surface, near the right edge, of the micro-sensor module 50. The electrical contact 114 provides a sensor output for the capacitive micro-sensor 102 and the reference micro-sensor 104. The electrical contact 114, as well as the common bottom plate 106 and the metal mesh top plate 110 can be made of one or more metals (e.g., aluminum, copper, alloys thereof, or other suitable interconnect metals), each having a thickness of about 0.5 µm.

A scribe line 115 is shown at the left edge.

Additional details in the processing of environmental micro-sensors such as the micro-sensors 102 and 104 can be found in U.S. patent application Ser. No. 13/853,732, which is incorporated by reference in its entirety.

Figure 6:
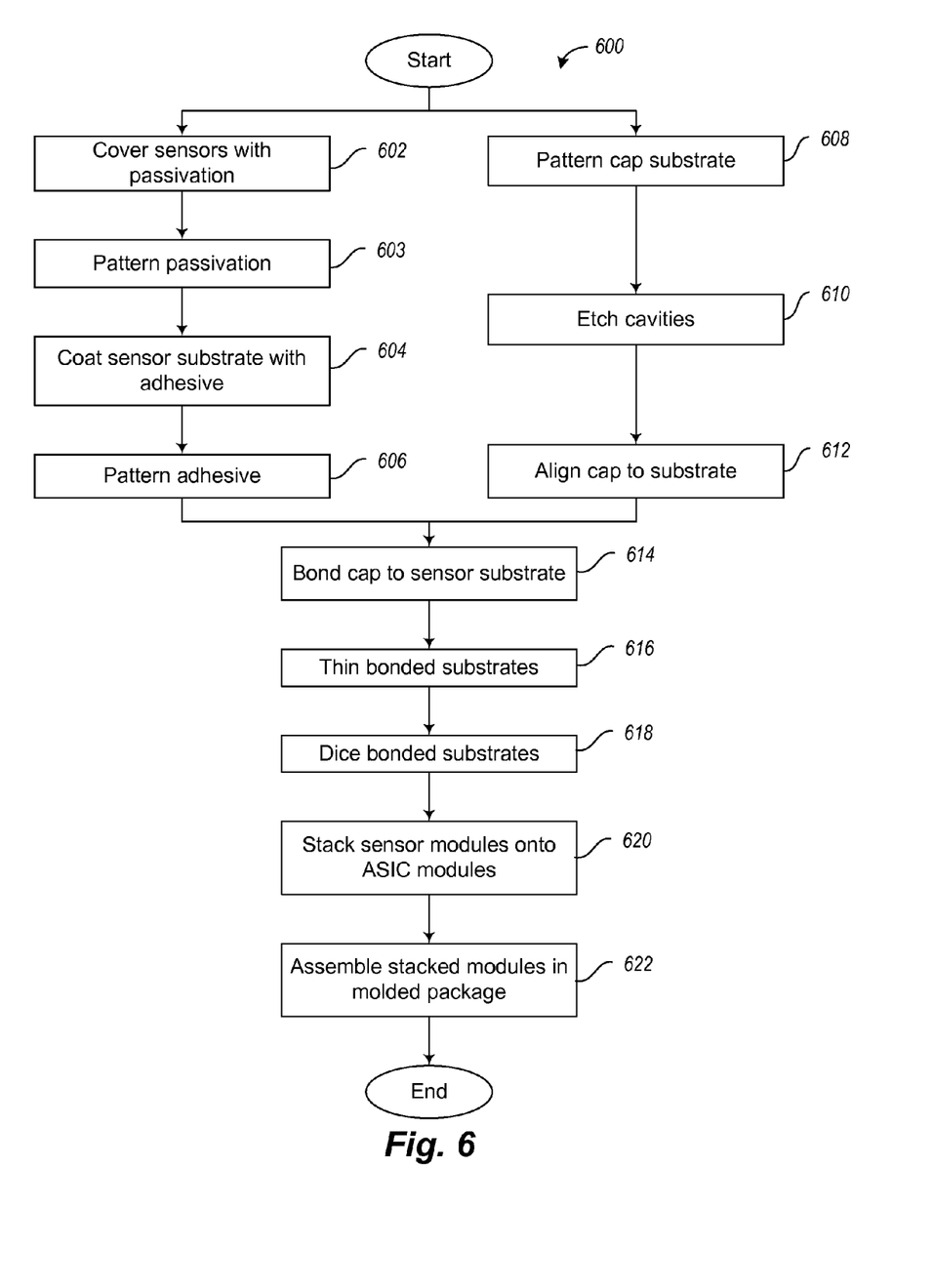
FIG. 6 is a detailed flow diagram showing a sequence of steps in fabricating a micro-sensor device, as described herein.

With reference to FIGS. 5-9, a sequence of processing steps 600, shown in FIG. 6, illustrates passivation of the micro-sensor modules 50, bonding to the caps 116, and assembling the micro-sensor modules 50 into a molded electronic package.

At 602, a conformal passivation layer 142 can be deposited over the micro-sensors 102 and 104. The passivation layer 142 can take the form of, for example, a 0.5 µm thick polyimide film. As is known to those skilled in the art, polyimide is a photo-sensitive material, similar to photoresist, that can be dispensed, spun to coat a substrate evenly, and patterned by exposing and developing away selected areas.

At 603, the conformal passivation layer 142 can be patterned to include an opening 143 in the capacitive micro-sensor 102, but not in the micro-sensor 104. The opening 143 extends through the conformal passivation layer 142, and through the underlying metal mesh top plate 110, partially into the dielectric active element 108. The opening 143 serves to expose the dielectric active element 108 to the ambient environment. Additional portions of the conformal passivation layer are patterned and removed so as to expose the electrical contacts 114.

At 604, an adhesive 144 is deposited, to which the cap 116 is later attached. In one embodiment, the adhesive 144 is a 10-μm thick layer of un-cured polyimide of the same type (e.g., HD 8820) used for the dielectric active elements 108. Use of the same, or a similar, material for both the dielectric active elements 108 and the adhesive 144 ensures chemical compatibility with the dielectric active elements 108 to prevent contamination. In addition, use of the same or a similar material helps to preserve mechanical stability of the dielectric active elements 108, which determine performance of the micro-sensor modules 50. The adhesive 144 is thus dispensed and spun to coat the sensor substrate 141. Alternatives to using polyimide as the adhesive 144 include dry resist or screen printing. Such options are disadvantageous, however, because they require additional tooling for depositing the material. Whereas, polyimide is a common material used for other layers, so it is readily available in most semiconductor fabrication facilities.

At 606, the adhesive 144 is patterned to cover the reference micro-sensor 104, but not the capacitive micro-sensor 102. Typically, such a material is cured by exposure to ultraviolet (UV) light, to harden the material. However, when used in the present application, the adhesive 144 desirably is patterned without curing, to retain adhesive properties of the polyimide film.

Figure 7:
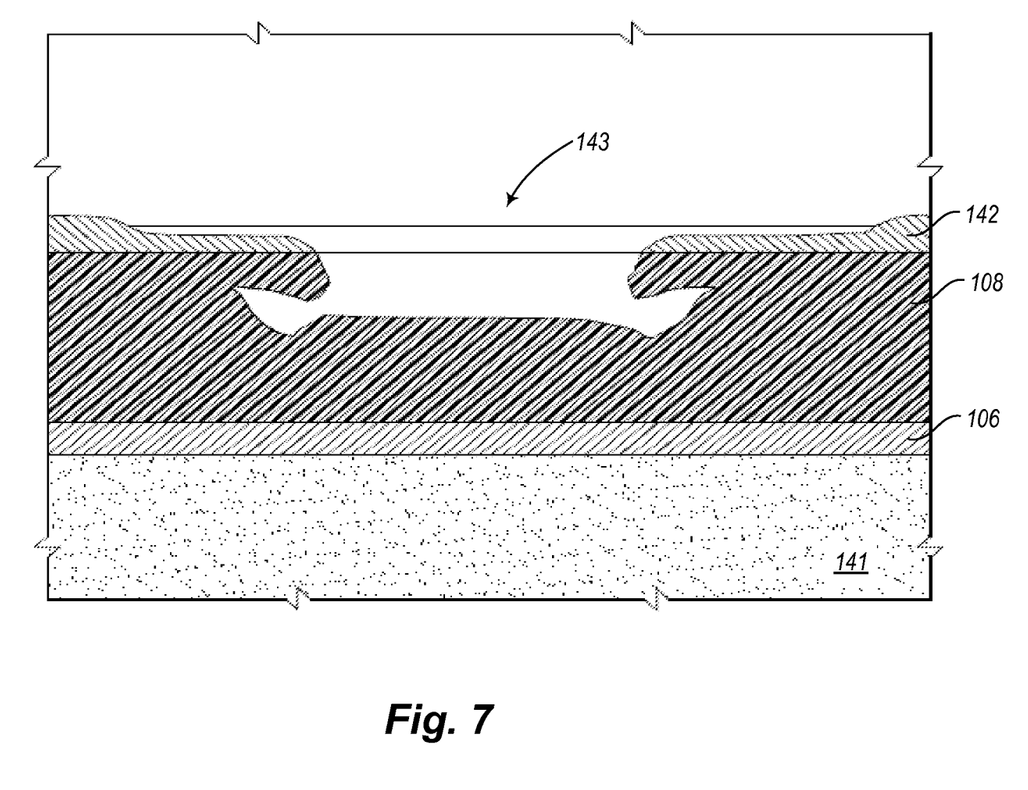
FIG. 7 is a magnified side view of an opening that exposes to an ambient environmental sensing element of a micro-sensor.

FIG. 7 shows a magnified view of the opening 143. It is noted that, when deposited, the adhesive 144 does not flow into the opening 143. If the adhesive 144 were to flow into the opening 143, the polyimide film (adhesive 144) would not be properly developed. In such an application, the uncured polyimide, which has low viscosity, exhibits low penetration and poor adhesion to the topography within the opening 143, thus preserving the sensing area of the dielectric active element 108. Because the polyimide exhibits such characteristics, the opening 143 can be made about 2 μm deep and about 8 μm wide without risk that the adhesive 144 will enter the opening 143. Furthermore, because it is so thick, the adhesive 144 serves also to planarize the micro-sensor structure which represents about a 4-6 μm step above the sensor substrate 141. After depositing the adhesive 144, a total sensor substrate thickness 145, in the example described, is about 675 μm.

Figure 8:
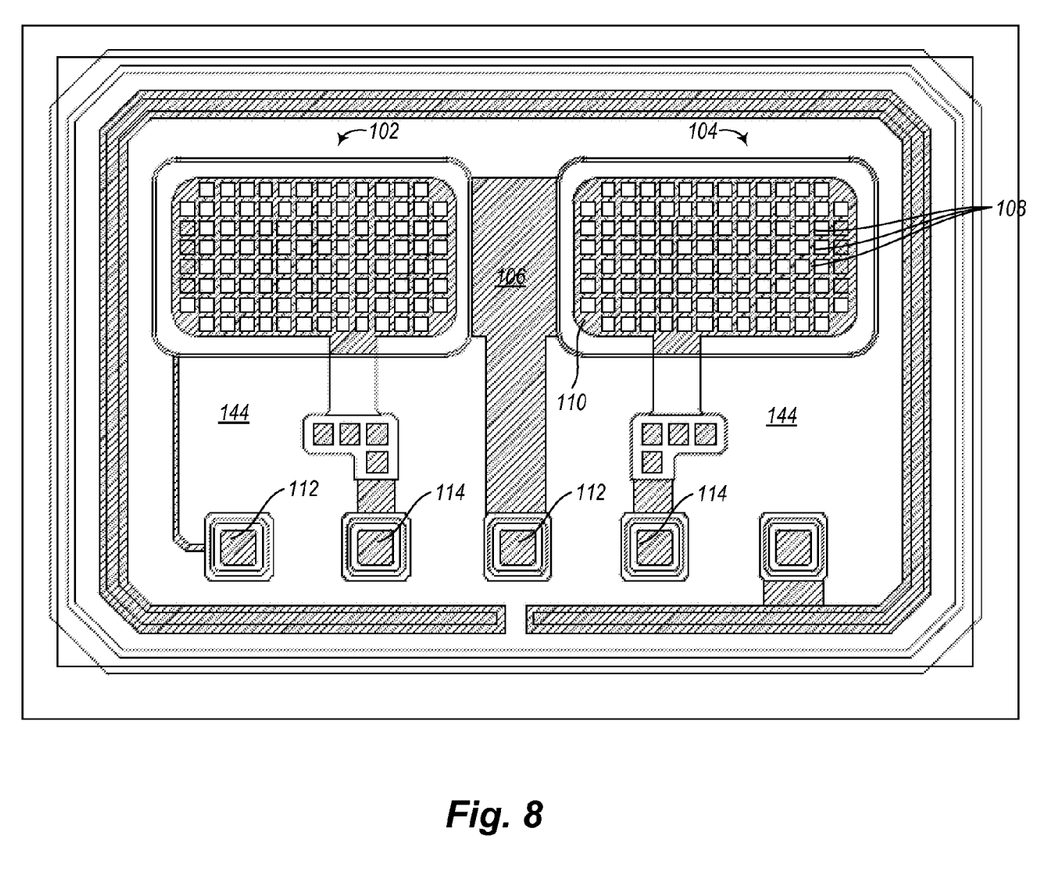
FIG. 8 is a top plan view of a micro-sensor module prior to bonding cap wafer as described herein.

FIG. 8 shows a top plan view of the micro-sensor module 50 following formation of the adhesive 144. With the adhesive 144 in place, use of the physical ring 64 is unnecessary.

Figure 9A:
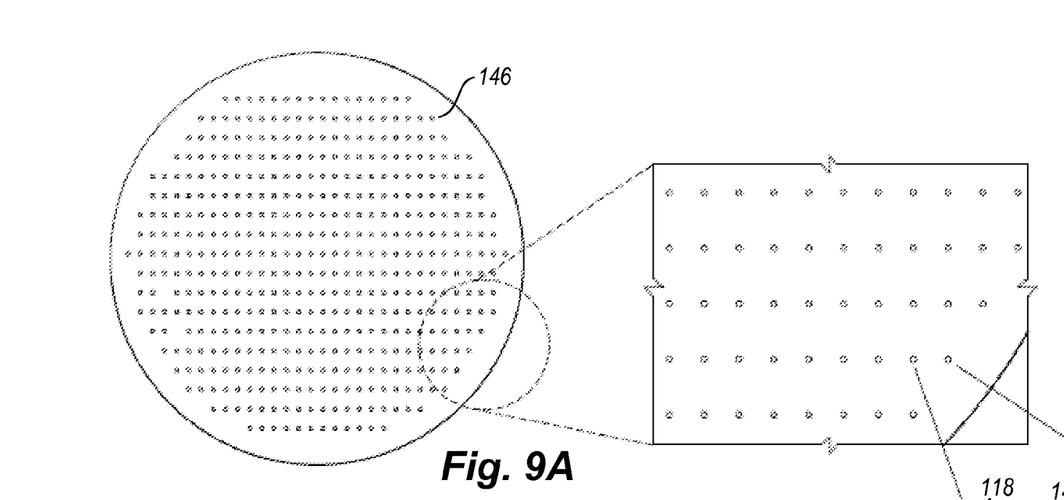
FIG. 9A is a top plan view of a patterned cap substrate.
Figure 9B:
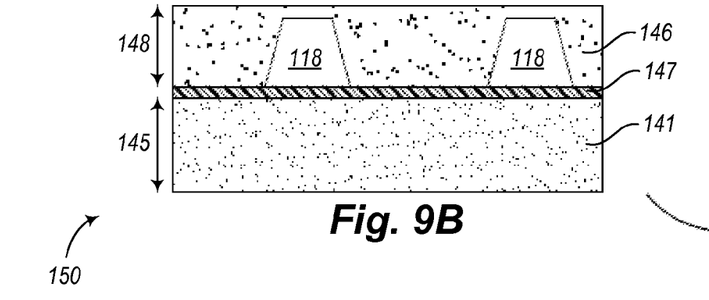
FIG. 9B is a side view of a patterned cap substrate bonded to a sensor substrate.
Figure 9C:
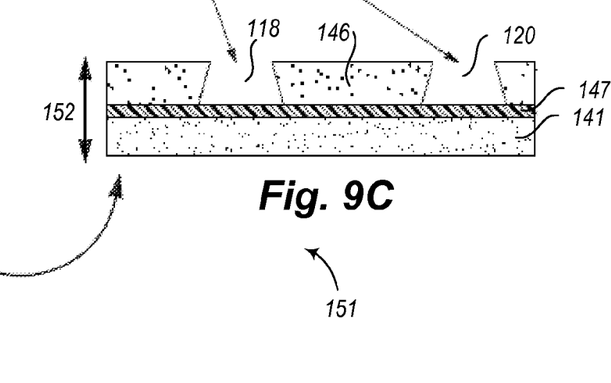
FIG. 9C is a side view of the bonded substrates shown in FIG. 9B, after thinning.

With reference to FIGS. 9A-9C, separate from processing the sensor substrate 141, a cap substrate 146 having a cap substrate thickness 148 can be prepared for bonding to the sensor substrate 141 (FIG. 9A). The cap substrate 146 can be, for example, a silicon substrate or a glass substrate. The cap substrate thickness 148 can be, for example, about 565 μm.

At 608, the cap substrate 146 can be patterned such that the sensor windows 118 and the contact windows 120 are etched through almost the entire thickness of the cap substrate, about 350 μm. Patterning of the sensor windows 118 and the contact windows 120 can be accomplished using a conventional patterning process that uses a photoresist mask and, for example, a wet chemical etchant that has a high etch rate. If the cap substrate 146 is made of glass, the etchant can be hydrofluoric acid (HF). If the cap substrate is made of silicon, the etchant can be, for example, potassium hydroxide.

At 612, the cap substrate 146 can be aligned to the sensor substrate 141 so that the sensor windows 118 are aligned with the micro-sensors 102, and the contact windows 120 are aligned with areas of the sensor substrate 141 in which the electrical contacts 112 and 114 are located. Use of a glass cap substrate 146 can facilitate the alignment process.

At 614, with the patterned adhesive 144 in place, the patterned cap substrate 146 can be inverted and bonded to the sensor substrate 141 to create a bonded structure 150 as shown in FIG. 9B, using a high-pressure bonding process. The bonded structure 150 includes the sensor substrate 141, a combined layer 147 that includes the sensor elements and the patterned adhesive 144, and the cap substrate 146. The bonding process can be carried out in a vacuum chamber that is heated to about 300° C. such that the bonding temperature remains below a characteristic temperature of the adhesive 144. Such a bonding temperature can cure the adhesive 144 during the bonding process. During the bonding process, pressure can be applied to the cap 116 for a time interval of about 30 minutes to 1 hour. The pressure can be applied using a piston that contacts the cap substrate 146 with, for example, 7000 Newtons of force. Other bonding process conditions, or alternative bonding processes can be substituted for those described herein.

Figure 10:
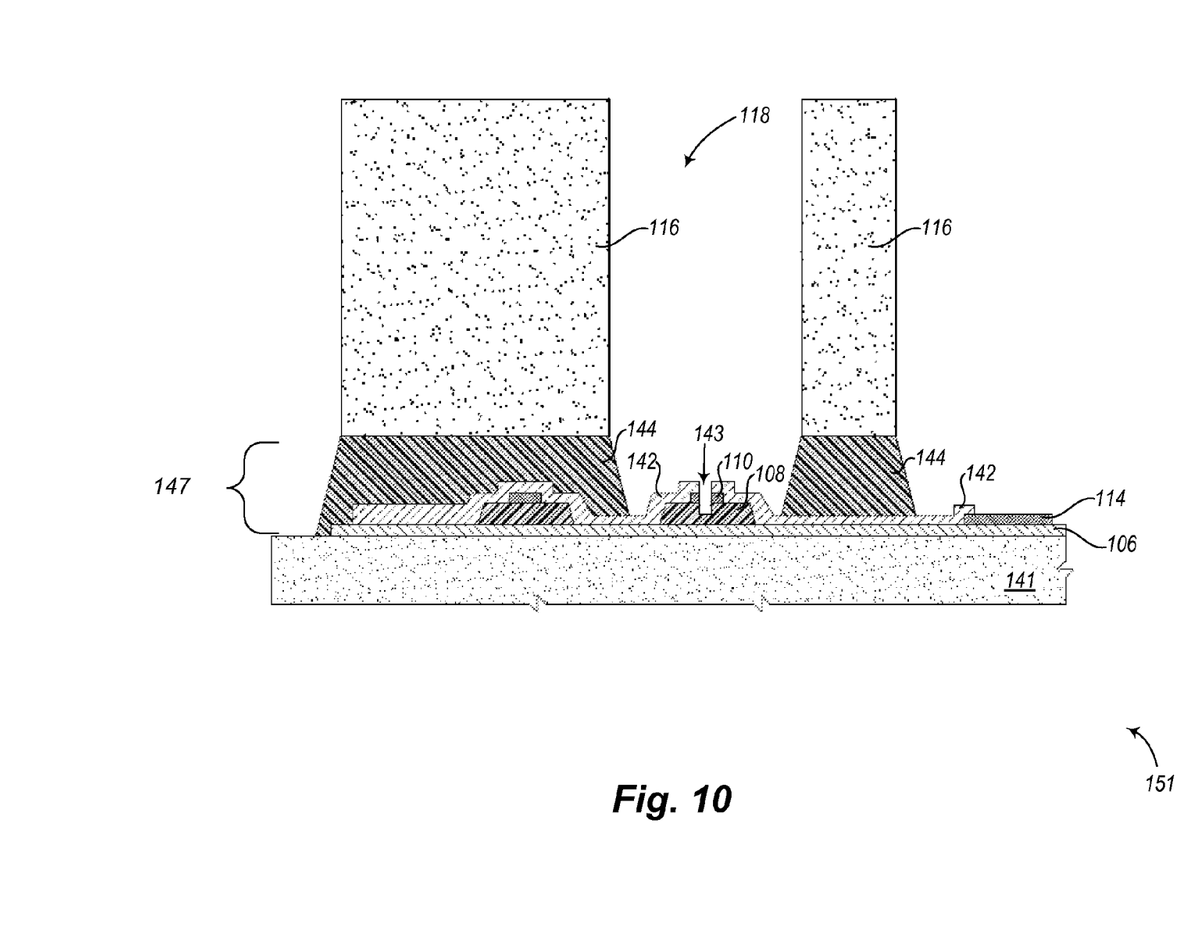
FIG. 10 is a magnified side view of the bonded substrates shown in FIG. 9C.

At 616, the bonded structure 150 can be thinned on both sides to produce a thin bonded structure 151 that is more compact and easier to package. In the thin bonded structure 151, the sensor substrate thickness 145 is reduced and the cap substrate thickness 148 is also reduced, thereby opening the sensor windows 118 and the contact windows 120. A bonded structure thickness 152 measures about 900 μm. The thinning process can subject the bonded structure 150 to a high degree of stress by grinding the surfaces of the bonded structure 150, using a chemical-mechanical polishing (CMP) slurry, or by use of a similarly abrasive process. The thin bonded structure 151 shown in FIG. 9C is also shown as a magnified side view in FIG. 10.

At 618, the bonded structure 150 can be sawed into individual micro-sensor modules 50 along scribe lines 115.

At 620, each micro-sensor module 50 can be stacked onto an ASIC module 52 to form a stacked sensor module.

At 622, the stacked sensor module can be assembled into a molded package by encapsulation using, for example, the epoxy molding compound 60.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of bonding a cap substrate to a sensor substrate, the method comprising:
   covering the sensor substrate with a passivation layer;
   patterning the passivation layer to expose bonding regions of the sensor substrate
   dispensing a volume of a photo-sensitive adhesive so that the photo-sensitive adhesive flows into the bonding regions to coat the sensor substrate, the photo-sensitive adhesive made of an electrically insulating material;
   patterning the photo-sensitive adhesive;
   patterning the cap substrate;
   aligning the cap substrate to the sensor substrate; and
   applying pressure to the cap substrate, the photo-sensitive adhesive, and the sensor substrate at a temperature that is lower than a characteristic temperature of the photo-sensitive adhesive, to bond the cap substrate to the sensor substrate using the electrically insulating material to electrically isolate the cap substrate from the sensor substrate.

2. The method of claim 1, further comprising etching cavities in the sensor substrate prior to aligning the cap substrate to the sensor substrate.

3. The method of claim 1, wherein the sensor substrate includes capacitive micro-sensors.

4. The method of claim 1, further comprising thinning the bonded substrates.

5. The method of claim 4, further comprising:
   dicing the thinned bonded substrates into micro-sensor modules;
   stacking each micro-sensor module onto an ASIC module; and
   assembling the stacked modules in a molded package.

6. A method of bonding a cap substrate to a sensor substrate, the method comprising:
   covering the sensor substrate with a passivation layer;
   patterning the passivation layer to expose bonding regions of the sensor substrate
   dispensing a volume of a photo-sensitive adhesive so that the photo-sensitive adhesive flows into the bonding regions to coat the sensor substrate,. the photo-sensitive adhesive made of an electrically insulating material;
   patterning the photo-sensitive adhesive;
   patterning the cap substrate;
   aligning the cap substrate to the sensor substrate; and
   applying pressure to the cap substrate, the photo-sensitive adhesive, and the sensor substrate at a temperature that is lower than a characteristic temperature of the photo-sensitive adhesive to bond the cap substrate to the sensor substrate;
   thinning the bonded substrates;
   dicing the thinned bonded substrates into micro-sensor modules;
   stacking each micro-sensor module onto an ASIC module;
   assembling the stacked modules in a molded package, the assembling including:
      encapsulating the stacked modules using an epoxy molding compound; and
      wire-bonding the micro-sensor module and the ASIC module to one another and to a semiconductor substrate.

7. The method of claim 1, wherein the photo-sensitive adhesive planarizes the capacitive micro-sensors.

8. The method of claim 1, wherein the cap substrate is a patterned silicon substrate.

9. The method of claim 1, wherein the cap substrate is a patterned glass substrate.

10. The method of claim 3, wherein one or more of the capacitive micro-sensors includes an environmentally-sensitive dielectric active element.

11. The method of claim 10, wherein the cap substrate has openings that expose the dielectric active element to an ambient environment.

12. The method of claim 10, wherein the photo-sensitive adhesive is made of substantially the same material as the dielectric active element.

13. The method of claim 10, wherein the photo-sensitive adhesive is chemically compatible with the dielectric active elements.

14. The method of claim 12, wherein the photo-sensitive adhesive is made of polyimide.

15. A method of bonding a cap substrate to a sensor substrate, the method comprising:
   covering the sensor substrate with a passivation layer;
   patterning the passivation layer to expose bonding regions of the sensor substrate
   dispensing a volume of a photo-sensitive adhesive so that the photo-sensitive adhesive flows into the bonding regions to coat the sensor substrate, the photo-sensitive adhesive made of an electrically insulating material;
   patterning the photo-sensitive adhesive;
   patterning the cap substrate;
   aligning the cap substrate to the sensor substrate; and
   applying pressure to bond the cap substrate, to the sensor substrate using the photo-sensitive adhesive, at a temperature that is lower than a characteristic temperature of the photo-sensitive adhesive;
   dicing the bonded substrates into micro-sensor modules;
   stacking each micro-sensor module onto an ASIC module;
   encapsulating the stacked modules using an epoxy molding compound; and
   wire-bonding the micro-sensor module and the ASIC module to one another and to a semiconductor substrate.

* * * * *

UNITED STATES PATENT AND TRADEMARK OFFICE
CERTIFICATE OF CORRECTION

| | |
|---|---|
| PATENT NO. | : 9,082,681 B2 |
| APPLICATION NO. | : 13/853886 |
| DATED | : July 14, 2015 |
| INVENTOR(S) | : Olivier Le Neel et al. |

It is certified that error appears in the above-identified patent and that said Letters Patent is hereby corrected as shown below:

In the Claims

Column 9, Line 6:
"regions to coat the sensor substrate,. the photo-sensitive" is incorrect, the correct line should read,
--regions to coat the sensor substrate, the photo-sensitive--.

Signed and Sealed this
Sixteenth Day of February, 2016

Michelle K. Lee
*Director of the United States Patent and Trademark Office*